United States Patent
Mitch

(10) Patent No.: US 7,442,671 B2
(45) Date of Patent: Oct. 28, 2008

(54) O-PHENYLPHENOL/ALKOXYLATED AMINE WOOD PROTECTION COMPOSITIONS

(75) Inventor: Eugene L. Mitch, Portland, OR (US)

(73) Assignee: Contechem Inc., Portland, OR (US)

( * ) Notice: Subject to any disclaimer, the term of this patent is extended or adjusted under 35 U.S.C. 154(b) by 619 days.

(21) Appl. No.: 10/900,835

(22) Filed: Jul. 27, 2004

(65) Prior Publication Data

US 2006/0025308 A1 Feb. 2, 2006

(51) Int. Cl.
*A01N 3/00* (2006.01)
*A61K 31/66* (2006.01)
*C09D 191/00* (2006.01)
*C09K 3/00* (2006.01)
*A01N 3/02* (2006.01)
*A01N 57/00* (2006.01)
*C09J 201/00* (2006.01)
*B01D 17/05* (2006.01)

(52) U.S. Cl. .................. 504/114; 514/104; 514/975; 516/168; 106/169.5

(58) Field of Classification Search ................ 504/114; 514/231, 667, 104, 975; 516/168; 106/169.51
See application file for complete search history.

(56) References Cited

U.S. PATENT DOCUMENTS 6,383,984 B1 * 5/2002 Aven ...................... 504/116.1
6,547,864 B1 * 4/2003 West ...................... 106/18.32

FOREIGN PATENT DOCUMENTS

EP 1273233 A1 * 1/2003

OTHER PUBLICATIONS

Ernest E. Hubert, The Preservative Treatment of Millwork, 1938, Journal of Industiral and Engineering Chemistry, vol. 30, No. 11, pp. 1241-1250.*

* cited by examiner

*Primary Examiner*—Johann Richter
*Assistant Examiner*—Andriae M Holt

(57) ABSTRACT

A composition for protecting wood from decay, mildew and sapstain comprises o-phenylphenol in combination with an alkoxylated amine, wherein the weight ratio of alkoxylated amine to o-phenylphenol ranges from 1:1 to 10:1. Organic or inorganic acids may be added to enhance solubility of the alkoxylated amines.

7 Claims, No Drawings

O-PHENYLPHENOL/ALKOXYLATED AMINE WOOD PROTECTION COMPOSITIONS

BACKGROUND OF THE INVENTION

This invention relates to the protection of wood products from decay, mildew and sapstain, and more particularly to compositions for effecting such protection.

Many compositions for protecting wood products have been proposed and used heretofore. Typical of such compositions are those disclosed in the following patents:

U.S. Pat. No. 6,576,629 Oppong, et al.: The combination of propiconazole and N-alkylheterocyclic compound, its salts or mixtures thereof, is employed to reduce the growth of microorganisms.

U.S. Pat. No. 6,547,864 to West: The combination of zinc oxide and dimethylalkylamine salts and monocarboxylic acids is used from protecting wood from decay, mildew, sapstain and ultraviolet light degradation.

U.S. Pat. No. 6,448,279 to Tseng, et al: A preservative composition comprising an amine oxide and an isothizolone is disclosed.

U.S. Pat. No. 6,211,218 to Goettsche, et al.: A wood preservative containing a dimethyalkylamine, an aliphatic dicarboxylic acid and a triazole compound is disclosed.

U.S. Pat. No. 4,950,685 to Ward: This patent discloses a wood preservative comprising a quaternary ammonium compound and 3-iodo-2-propyl butyl carbamate, providing stain resistance to wood.

U.S. Pat. No. 4,380,561 to Sundman, et al.: Branched-chain aliphatic carboxcylic acids, or their alkali-or amonium salts are disclosed for use in protecting wood against attack of sapstain and mold fungi.

International application No. WO 03/065807 discloses formulations comprising triazoles and alkoxylated amines as wood preservatives.

The foregoing evidences that there is a wide variety of wood preservative compositions alleged to be effective in the protection of wood. However, none of these discloses the simplified and effective compositions of this invention.

SUMMARY OF THE INVENTION

This invention comprises a combination of o-phenylphenol and an alkoxylated amine as an effective composition for protecting wood from decay, mildew and sapstain. Various additives may be used to achieve specific results.

The principal objective of this invention is the provision of a composition for protecting wood, which consists essentially of o-phenylphenol and an alkoxylated amine. "Consisting essentially of" is defined as limited to the specified compounds of the claim which do not materially affect the nature of the composition and would allow for the addition of a buffer solution as defined later in the specification.

Another objective of this invention is to provide improved wood protection with an emulsifiable concentrate of o-phenylphenol enhanced in activity with an alkoxylated amine and exhibiting a pH of 2 to 9 in dilute solution.

A further objective of this invention is the provision of a composition of the class described which is simplified in its basic constituents and allows for variations thereof for selected purposes.

The foregoing and other objectives of this invention will appear from the following detailed description of the preferred embodiments.

DESCRIPTION OF THE PREFFERED EMBODIMENTS

In its basic concept this invention relates to the preparation and use of water dispersible o-phenylphenol wood preservatives and sapstain control chemicals. Specifically, this invention relates to a wood preservative composition consisting essentially of o-phenylphenol and alkoxylated amines. The formulations may include organic or inorganic acids to enhance the solubility of the alkoxylated amines.

O-phenylphenol is well known as a disinfectant, sanitizer and fungicide. It is only slightly soluble in water, but is soluble in most organic solvents and oils. It can be formulated with the aid of anionic emulsifiers; however it is generally incompatible with most other types of surfactants and emulsifiers. For wood preservation, o-phenylphenol is commercially used in the form of its sodium salt. Wood treatment solutions of sodium o-phenylphenate must be maintained at pH 10.0-11.0 for solution stability. The elevated pH may cause darkening or discoloration of some wood species.

Alkoxylated amines are surface-active agents that may be used as emulsifiers for water insoluble chemicals. Alkoxylated amines also are known to enhance the activity of fungicidal formulations comprising fungicidal triazoles. However this invention does not pertain to triazoles. This invention does pertain to emulsifiable concentrates comprising o-phenylphenol and alkoxylated amines. The formulations of this invention may include acids to enhance the stability of emulsifiable concentrates when diluted in water.

This invention discloses a composition for protecting wood from decay, mildew and sapstain, which comprises o-phenylphenol in combination with an alkoxylated amine of the following formula (I):

$$R^1—N—[CH_2CH(X)O]_aH$$
$$|$$
$$R^2$$

Wherein $R^1$ is a $C_{8-20}$ alkyl; $R^2$ is 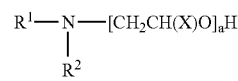 $—[CH_2CH(X)O]_bH$ Or

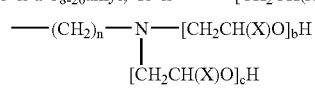
$—(CH_2)_n—N—[CH_2CH(X)O]_bH$
$|$
$[CH_2CH(X)O]_cH$ n is an integer from 1 to 4;

each a,b,c independently are integers which may vary from 1 to 20;

each X independently is selected from the group consisting of hydrogen, methyl, ethyl, and phenyl.

The preferred embodiment of this invention relates to wood protection compositions prepared by blending o-phenylphenol with an alkoxylated amine, preferably the formula (I) identified above, wherein one or more of the following restrictions apply:

a) n is an integer 2 or 3, preferably 3.
b) X is hydrogen
c) $R^1$ is a $C_{10-20}$ alkyl, preferably cocoalkyl or tallowalkyl
d) The most preferred alkyl is N,N',N'-tris-(2-hydroxyethyl)-N-tallowalkyl-1,3-diaminopropane.

The relative weight ratio of alkoxylated amine to o-phenylphenol is 1:1 to 9:1, preferably 3:1 to 5:1.

The compositions of this invention may be applied to a substrate as a concentrate, or preferably as a dispersion in water, by conventional means such as by brush, spray, immersion or pressure. Before application the concentrate preferably is dispersed or diluted with water to a 0.1% to 0.5% concentration of o-phenylphenol.

The addition of 1 to 10 percent by weight, preferably 4 to 6 percent by weight, of a monocarboxylic acid containing one to four atoms to the blend enhances the stability of the dilute solution. Alternatively, the dispersion may be acidified with other acids to pH 1 to pH 7, preferably pH 4-6 with water. It is advantageous to use an acidic iron stain inhibitor to adjust the pH after dilution with water.

A preferred embodiment of this invention is as follows:

1) Twenty (20) parts by weight of o-phenylphenol and eighty (80) parts by weight of the above most preferred alkoxylated amine were blended at moderate temperature (50-60 degrees centigrade) to give a homogeneous solution used in the Table I set forth below.

2) One part of the above composition was diluted with fifty parts of water to give a milky unstable dispersion, pH 7-8, containing 0.4% o-phenylphenol.

3) The unstable dispersion was acidified with SOLBRITE E, a proprietary iron stain inhibitor, until it became clear, pH 4-5 (SOLUTION A in the following Table).

4) BRITEWOOD S, SAPSTAIN CONTROL, is a commercial formulation containing 23% by weight of sodium o-phenylphenate, equivalent to 20% o-phenylphenol.

5) One part of BRITEWOOD S was diluted with 50 parts of water to give a clear stable solution, pH 10-11, containing 0.4% o-phenylphenol (SOLUTION B in the following Table).

Evaluation of the foregoing preferred ingredient was conducted by immersing a 12" portion of one end of a 1"×4"×4' piece of freshly cut Douglas fir in the foregoing treating solutions (steps 3 and 5) for 30 seconds. This specimen was lifted from the solution and allowed to drain for 30 seconds. Thirty replicate pieces of wood were treated in the same manner with SOLUTION A AND SOLUTION B. The treated pieces were close piled on a pallet along with other test pieces, surrounded by untreated wood, covered with black plastic and stored in a shady location in Oregon during August, September and October, 2003.

The wood specimens were evaluated after 30 and 90 days. The treated and untreated areas were rated on a scale of 1-10, where 1 is less than 10% and 10 is 100% discoloration, mold and sapstain. A rating of less than one is commercially acceptable. A rating of two is marginal, and above two results in significant downgrading in value or rejection for commercial use.

TABLE I

| TIME | SOLUTION A Average Rating | SOLUTION B Average Rating | UNTREATED Average Rating |
|---|---|---|---|
| 30 DAYS | 0 | 2 | 9-10 |
| 90 DAYS | >1 | 2+ | 10 |

From the foregoing it will be appreciated that the foregoing compositions of this invention comprising o-phenylphenol and an alkoxylated amine are simplified compositions which are inexpensive to manufacture and are superior to prior formulations for this purpose.

It will be apparent to those skilled in the art that various changes may be made in the formulations described hereinbefore without departing from the spirit of this invention and the scope of the appended claims.

I claim:

1. A composition for protecting freshly cut Douglas fir from sapstain, consisting essentially of an aqueous emulsion containing 0.1 to 0.5 weight percent of o-phenylphenol and an alkoxylated amine in a weight ratio of 1:1 to 9:1 relative to the weight of o-phenylphenol.

2. The composition of claim 1 wherein the alkoxylated amine has the formula

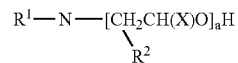

wherein $R^1$ is a $C_{8-20}$ alkyl and $R^2$ is $-[CH_2CH(X)O]_bH$ and a and b are integers ranging from 1 to 20, and X is selected from the group consisting of hydrogen, methyl, ethyl and phenyl.

3. The composition of claim 2 wherein $R^2$ is

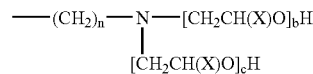

n is an integer from 1 to 4, each a,b,c are integers ranging from 1 to 20, and X is selected from the group consisting of hydrogen, methyl, ethyl and phenyl.

4. The composition of claim 2 wherein $R^1$ is cocoalkyl.

5. The composition of claim 2 wherein $R^1$ is tallowalkyl.

6. The composition of claim 5 wherein $R^2$ is N,N$^1$,N$^1$-tris-(2-hydroxyethyl)-N-tatlowalkyl-1,3-diaminopropane.

7. The composition of claim 1 further comprising a monocarboxcylic acid.

* * * * *